US012156953B2

(12) United States Patent
Padula et al.

(10) Patent No.: US 12,156,953 B2
(45) Date of Patent: Dec. 3, 2024

(54) SANITIZATION SYSTEM AND METHOD

(71) Applicant: Orbital Building Solutions, Inc., Philadelphia, PA (US)

(72) Inventors: Vincent Padula, West Chester, PA (US); Stephen McCrossin, Havertown, PA (US); Alexander Hammelbacher, Media, PA (US)

(73) Assignee: Orbital Building Solutions, Inc., Philadelphia, PA (US)

( * ) Notice: Subject to any disclaimer, the term of this patent is extended or adjusted under 35 U.S.C. 154(b) by 0 days.

(21) Appl. No.: 18/119,664

(22) Filed: Mar. 9, 2023

(65) Prior Publication Data
US 2023/0201394 A1    Jun. 29, 2023

Related U.S. Application Data

(62) Division of application No. 17/069,259, filed on Oct. 13, 2020, now Pat. No. 11,617,812.

(60) Provisional application No. 63/024,618, filed on May 14, 2020.

(51) Int. Cl.
*A61L 2/22* (2006.01)
*A61L 2/24* (2006.01)

(52) U.S. Cl.
CPC ............... *A61L 2/22* (2013.01); *A61L 2/24* (2013.01); *A61L 2202/14* (2013.01); *A61L 2202/15* (2013.01); *A61L 2202/25* (2013.01)

(58) Field of Classification Search
CPC .................................... A61L 2/24; A61L 2/22
See application file for complete search history.

(56) References Cited

U.S. PATENT DOCUMENTS

| 5,993,739 | A | 11/1999 | Lyon | |
|---|---|---|---|---|
| 2011/0315175 | A1 | 12/2011 | Lella et al. | |
| 2015/0258233 | A1 | 9/2015 | Brown et al. | |
| 2016/0250368 | A1* | 9/2016 | Brown | A61L 2/208 422/110 |
| 2017/0014540 | A1* | 1/2017 | Kawasaki | F24F 8/24 |
| 2019/0105418 | A1 | 4/2019 | Jaques et al. | |
| 2019/0247529 | A1* | 8/2019 | Shane | A61L 2/22 |

OTHER PUBLICATIONS

Non-Final Office Action dated Dec. 28, 2022, issued in U.S. Appl. No. 17/069,259; 9 pages.
Notice of Allowance and Fees Due, dated Feb. 23, 2023, issued in U.S. Appl. No. 17/069,259; 8 pages.

* cited by examiner

*Primary Examiner* — Kevin Joyner
(74) *Attorney, Agent, or Firm* — Fresh IP PLC; John R. Bednarz

(57) ABSTRACT

An apparatus includes at least one storage tank configured to store a disinfectant/sanitization solution, at least one pump connected to the at least one storage tank to distribute the disinfectant/sanitization solution via a piping system, at least one valve in communication with the piping system to open and close to control flow of the disinfectant/sanitization solution, at least one device to control the flow of the disinfectant/sanitization solution for a particular period of time to at least one misting nozzle, and the at least one misting nozzle in communication with the piping system and the at least one valve to mist a particular area with the disinfectant/sanitization solution.

14 Claims, 3 Drawing Sheets

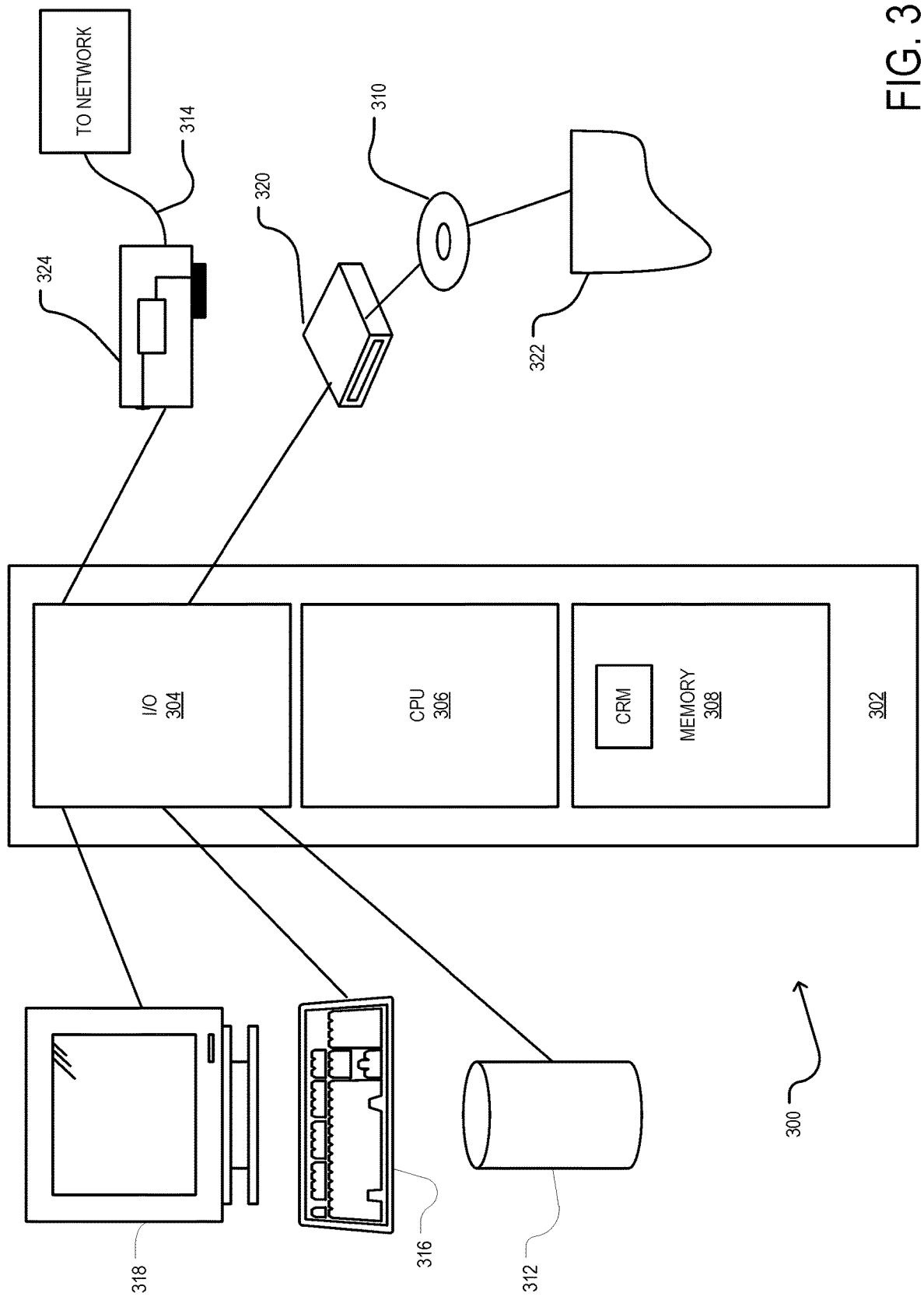

SANITIZATION SYSTEM AND METHOD

CROSS REFERENCE TO RELATED APPLICATIONS

This application is a divisional application that claims priority from application Ser. No. 17/069,259 entitled "SANITIZATION SYSTEM AND METHOD" filed Oct. 13, 2020, which claims priority from Application No. 63/024,618 entitled "Sanitization System and Method" filed May 14, 2020, the entire disclosure of which is incorporated herein by reference.

BACKGROUND

In late 2019 and early 2020, a novel infectious disease known as COVID-19 or known colloquially as coronavirus began infecting people throughout the world. COVID-19 is caused by a virus named SARS-CoV-2 that is believed to be spread by people who are in close contact with one another and droplets that may be associated with sneezing, coughing, or even talking. The droplets may fall onto a surface or onto the ground and may come in contact with a person. Although it is believed that people showing symptoms of the disease are contagious, the virus is also believed to be spread by asymptomatic individuals. The disease spread from China, to Europe, and to the United States and beyond rapidly resulting in a pandemic recognized by the World Health Organization (WHO) in March 2020.

A very large percentage of the world was forced into social distancing through mandatory lockdowns and stay-at-home orders to prevent the spread of this new virus. In March 2020, the United States began extended and unprecedented lockdowns and stay-at-home restrictions in a majority of the nation due to coronavirus. During the lockdowns and stay-at-home restrictions, public buildings and venues such as office buildings and schools have had to remain closed or off-limits for a long period of time. Although it is believed that a vaccine may not be available for twelve to eighteen months, it is simply not feasible for buildings to remain closed. Businesses, public venues, and public buildings are in the process of reopening and adjusting in an effort to protect occupants and employees from the coronavirus.

It is with these issues in mind, among others, that various aspects of the disclosure were conceived.

SUMMARY

According to one aspect, an engineered sanitization system includes an apparatus including at least one storage tank configured to store a disinfectant/sanitization solution, at least one pump connected to the at least one storage tank to distribute the disinfectant/sanitization solution via a piping system, at least one valve in communication with the piping system to open and close to control flow of the disinfectant/sanitization solution, at least one device to control the flow of the disinfectant/sanitization solution for a particular period of time to at least one misting nozzle, and the at least one misting nozzle in communication with the piping system and the at least one valve to mist a particular area with the disinfectant/sanitization solution.

According to another aspect, a method includes sending, by at least one processor, a command to at least one pump to begin operation, delivering, by the at least one pump, disinfectant/sanitization solution via a piping system to at least one misting nozzle, opening or closing at least one valve in communication with the piping system to control flow of the disinfectant/sanitization solution, controlling the flow of the disinfectant/sanitization solution by at least one device to the at least one misting nozzle for a particular period of time, and misting a particular area with the disinfectant/sanitization solution by the at least one misting nozzle for the particular period of time.

According to an additional aspect, a non-transitory computer-readable storage medium includes instructions stored thereon that, when executed by a computing device cause the computing device to perform operations, the operations including sending, by at least one processor, a command to at least one pump to begin operation, delivering, by the at least one pump, disinfectant/sanitization solution via a piping system to at least one misting nozzle, opening or closing at least one valve in communication with the piping system to control flow of the disinfectant/sanitization solution, controlling the flow of the disinfectant/sanitization solution by at least one device to the at least one misting nozzle for a particular period of time, and misting a particular area with the disinfectant/sanitization solution by the at least one misting nozzle for the particular period of time.

These and other aspects, features, and benefits of the present disclosure will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate embodiments and/or aspects of the disclosure and, together with the written description, serve to explain the principles of the disclosure. Wherever possible, the same reference numbers are used throughout the drawings to refer to the same or like elements of an embodiment, and wherein:

FIG. 3 illustrates a block diagram of a computing device according to an example embodiment.

DETAILED DESCRIPTION

Figure 1:
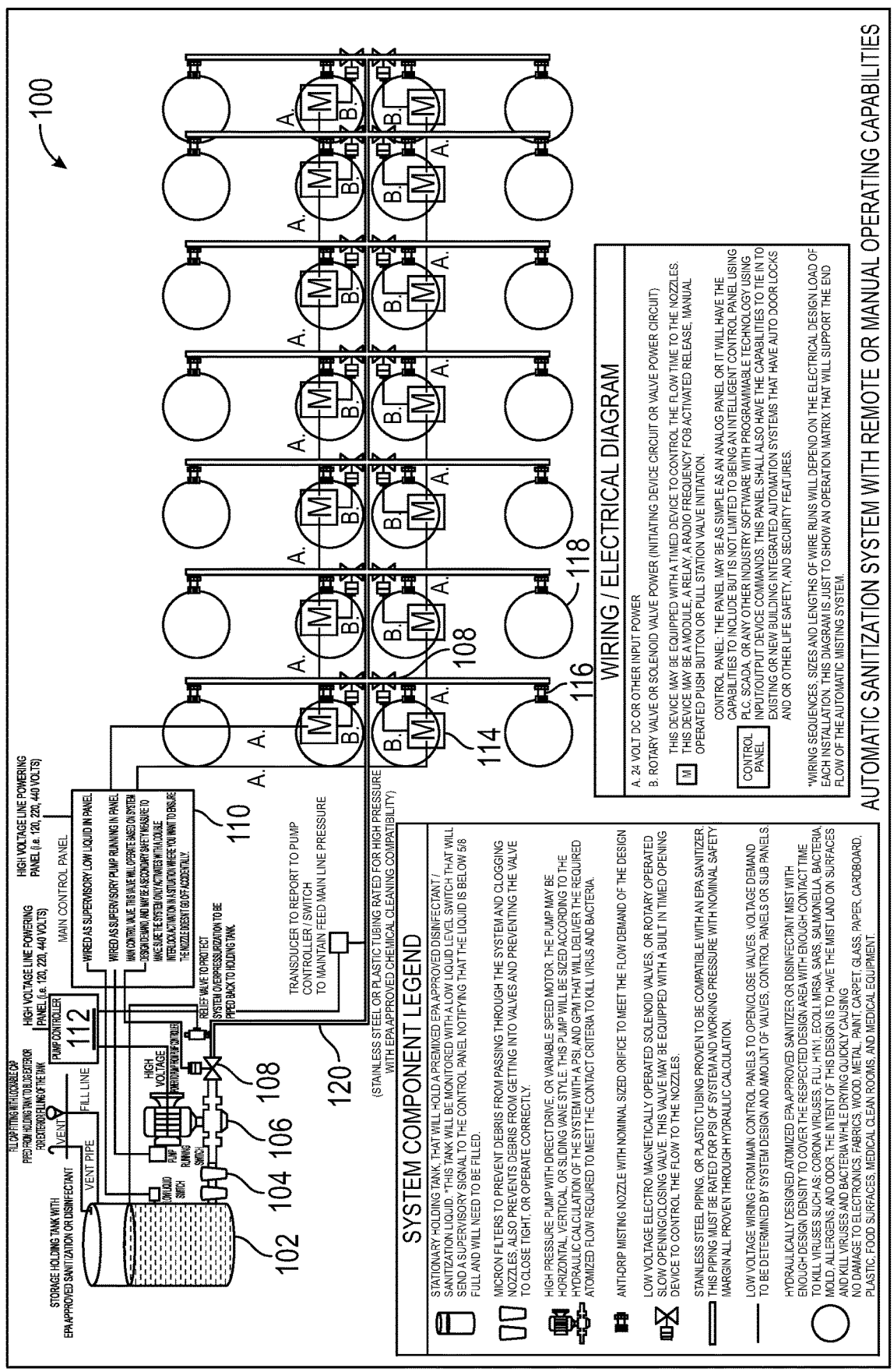
FIG. 1 is a block diagram of an engineered sanitization system according to an example embodiment.

Aspects of an engineered sanitization system and method includes an apparatus comprising at least one storage tank configured to store a disinfectant/sanitization solution, at least one pump connected to the at least one storage tank to distribute the disinfectant/sanitization solution via a piping system, at least one valve in communication with the piping system to open and close to control flow of the disinfectant/sanitization solution, at least one device to control the flow of the disinfectant/sanitization solution for a particular period of time to at least one misting nozzle, and the at least one misting nozzle in communication with the piping system and the at least one valve to mist a particular area with the disinfectant/sanitization solution.

The sanitization system may include at least one pump controller in communication with the at least one pump to provide power to the at least one pump. In addition, the sanitization system may include a control panel to provide commands to the at least one device to control the flow of the disinfectant/sanitization solution. The sanitization system may include at least one filter to prevent debris from passing through the apparatus. The sanitization system may be located in a building such as an industrial building, a commercial building, a school, a hospital, or another type of building. The disinfectant/sanitization solution may be approved by the United States Environmental Protection Agency (EPA). According to one example, the sanitization system may include at least one computing device to control the flow of the disinfectant/sanitization solution for the particular period of time to the at least one misting nozzle.

During the 2019-2020 coronavirus pandemic, countries throughout the world including China, Italy, Spain, and the United States instituted lockdowns and stay-at-home restrictions to keep people from spreading the disease. Because of the coronavirus pandemic, many public places and venues in the United States such as schools, hotels, gyms, buses, public transportation rail system vehicles and stations, daycares, nursing homes, hospitals, stadiums, auditoriums, amusement parks, public bathrooms, restaurants, manufacturing plants, offices, and other shared spaces had to shutter for an indefinite period of time. The stay-at-home orders have directly impacted every aspect of our society via school closures, business closures, and places of leisure being forced to close with an indefinite opening date. Associated buildings and venues do not know how to reopen safely and invite customers and consumers. Customers and consumers are unsure of when they may safely visit these venues and buildings that are struggling to reopen. Many of these venues and buildings are unable to appropriately clean, disinfect, and sanitize.

The sanitization system discussed herein will allow places to be sanitized/disinfected safely and efficiently through a permanently installed system on location at schools, hotels, gyms, buses, public transportation rail system vehicles and stations, daycares, nursing homes, hospitals, stadiums, auditoriums, amusement parks, public bathrooms, restaurants, manufacturing plants, duct work systems, offices, and other shared spaces that will be ready to go at the push of a button or through automatic operation at a specific time.

Conventional solutions may include people that are hired to manually mist, fog, or disinfect spaces by hand as a preventative maintenance measure under operating guidelines instituted by governmental authorities such as the CDC, NHS, or any other local, federal, or state jurisdiction or after there may have been an outbreak at a building. A company may have to pay salaries, travel expenses, insurance, vacation, and sick leave. In addition, crews that perform these functions manually may have to sanitize or disinfect on a daily, an hourly, or a weekly basis. The current solutions are not cost effective and may result in people becoming unnecessarily exposed to illness resulting in liability and lost revenue. Additionally, businesses may be forced to close while cleaning spaces by hand. The system discussed herein addresses these issues and provides a number of safety-related benefits through automation and building or space integration.

FIG. 1 shows a block diagram of an engineered sanitization system 100 according to an example embodiment. The sanitization system 100 includes at least one storage tank 102 that may hold or is configured to hold or store a disinfectant/sanitization solution or liquid. The disinfectant/sanitization solution may be a non-hazardous, non-flammable solution that will be stored in the at least one storage tank that may be a refillable, stationary monitored storage tank. In addition, the sanitization system 100 may include at least one filter 104 such as a micron filter that is configured to prevent debris from passing through the system 100 and clogging nozzles. The filter 104 may prevent debris from entering valves that may prevent the valves from closing or operating correctly.

In addition, the sanitization system 100 may include at least one high pressure pump 106 that may have a direct drive or variable speed motor. The pump 106 may be a horizontal, vertical, or sliding vane pump, among other types of pumps. The pump 106 may be sized according to a hydraulic calculation of the system and have a pound per square inch (PSI) and gallons per minute (GPM) that may deliver an atomized flow to meet contact criteria and kill viruses and bacteria, among others. The sanitization system 100 may include at least one pump controller 112 to control the pump 106. The at least one pump controller 112 may be connected to a high voltage line powered panel (e.g., one hundred and twenty, two hundred and twenty, four hundred and forty volts, among others).

The sanitization system 100 may include at least one anti-drip misting nozzle 116. The anti-drip misting nozzle 116 may have at least one nominal sized orifice to meet a flow demand of the system. The sanitization system 100 may include at least one valve 108 such as a solenoid valve that may be a low voltage electromagnetic solenoid valve. Alternatively, the valve 108 may be a rotary operated slow opening/closing valve. The valve 108 may be equipped or associated with a built-in timed opening device 114 to control the flow to the nozzles.

The sanitization system 100 may include a piping and/or tubing system 120 that may be used to transport and deliver the sanitizer. The piping system 120 may be capable of withstanding a particular pound per square inch (PSI). The piping of the piping system 120 may be non-corrosive stainless steel, copper tube, poly, or rubber tubing that is chemically compatible with an EPA approved solution.

The sanitization system 100 may include low voltage wiring that may be in communication with at least one main control panel 110 to operate the valves 108, e.g., open and close the valves. The main control panel 110 may be connected to a high voltage line powered panel (e.g., one hundred and twenty, two hundred and twenty, four hundred and forty volts, among others). The control panel 110 may be an analog control panel or an intelligent control panel. The intelligent control panel may include a programmable logic controller (PLC), a supervisory control and data acquisition (SCADA) system, or another type of computing device having software functionality such that it may be programmable to allow input/output device commands for the one or more valves 108 and nozzles 116.

As an example, software associated with the control panel 110 will allow the opening and closing of valves 108 through a programmed sequence of operations or an operations matrix designed for the specific needs of each installation in a building or a portion of a building. The control panel 110 may be associated with an existing building integrated automation system or a new building integrated automatic system that may provide automatic door locks and/or other life safety and security features. The sanitization system 100 may be electrically powered by a power source such as twenty-four volt direct current (DC) or another input power.

As shown in FIG. 1, each valve 108 and nozzle 116 may be associated with the device 114 such as a timed device to control flow time to the nozzle. The device 114 may be a module, a relay, a radio frequency fob device, a manually operated push button, or a pull station valve, among others. Each nozzle 116 may spray, fog, or mist a particular zone, region, or area 118. The zone, region, or area may be in a building or venue.

The nozzle 116 may provide hydraulically designed atomized EPA approved sanitizer or disinfectant mist or fog with enough design density to cover the particular zone, region, or area 118 with enough contact time to kill or eliminate viruses such as coronaviruses, flu viruses, influenza A virus subtype H1N1, *E. coli,* Methicillin-resistant *Staphylococcus aureus* (MRSA), Severe acute respiratory syndrome (SARS), *Salmonella,* bacteria, mold, allergens, and odor, among others. As a result, the mist or fog may land on surfaces and kill viruses and bacteria and dry quickly to eliminate damage to electronics, fabrics, wood, metal, paint, glass, paper, cardboard, plastic, food, surfaces, medical clean rooms, and medical equipment, among others. The sanitization system 100 may have one area or zone of activation or may operate specific zones one at a time or many zones at a time. As an example, the sanitization system 100 may be manually operated using one or more push buttons, one or more pulled switches, one or more wireless activated radio frequency switches controlled by a fob, and/or activated using a computing device such as a smart phone device.

Each nozzle 116 may be anti-drip with a closing PSI rating that will allow the nozzle to close while still in an atomizing pressure phase. This will prevent the nozzles 116 from closing and having the EPA approved solution still dripping from a nozzle 116 after the controlling valve 108 has closed and the operating pressure starts to decrease. The nozzles may be sized according to the hydraulic design of the system and a flow demand calculation may be based on an area, height, pipe sizes, fittings, and friction loss of the solution flowing to the nozzle to be atomized. The nozzles 116 may be supported by hydraulic demand calculation (Hazen Williams) or another calculation.

The sanitizer or disinfectant may be EPA-approved, non-flammable, environmentally safe, residue free, non-corrosive, National Sanitation Foundation (NSF) certified to be sprayed on food contact surfaces, timed specific to the required location and surface demand, odorless, fast drying, non-skin irritating, and most of all will give the world a safer place to gather with less risk of contamination.

The sanitization system 100 may include a vent pipe that is in communication with the at least one storage tank 102 and connected to a vent. In addition, the sanitization system 100 may include a fill cap fitting with a lockable cap that may connect the at least one storage tank 102 to a source that may be exterior to the sanitization system 100 such as a source outside of or exterior to a building associated with the sanitization system 100.

The sanitization system 100 may further include a low liquid/solution switch that may be activated when the at least one storage tank 102 is below a particular level of disinfectant/sanitization solution. The sanitization system 100 may also include a pump running switch to activate and deactivate the at least one pump 106.

The sanitization system 100 may also include at least one relief valve to protect system over-pressurization that is set a number of PSI above a typical system demand working and operating pressures. In the event that there is over-pressurization, the pressure may be relieved using the relief valve back to the at least one storage tank 102. The sanitization system 100 may further include at least one transducer in communication with the pump controller 112 to maintain a feed main line pressure.

The sanitization system 100 may include a manually operated control valve 122 and may include an inline check valve 124. The manually operated control valve 122 may be used to stop the system 100 during an emergency and may function as an emergency shut off valve. The manually operated control valve 122 may be used by a person or service, maintenance, repair, or inspection technician. The inline check valve 124 may open during flow and may close when flow stops to prevent back pressure from downstream pressure that could blow back into the storage tank 102.

The sanitization system 100 may be associated with a computing device that includes at least one processor to process data and memory to store data. The processor processes communications, builds communications, retrieves data from memory, and stores data to memory. The processor and the memory are hardware. The memory may include volatile and/or non-volatile memory, e.g., a computer-readable storage medium such as a cache, random access memory (RAM), read only memory (ROM), flash memory, or other memory to store data and/or computer-readable executable instructions. In addition, the at least one computing device further includes at least one communications interface to transmit and receive communications, messages, and/or signals.

The at least one computing device can be a laptop computer, a smartphone, a personal digital assistant, a tablet computer, a standard personal computer, or another processing device. The at least one computing device may include a display, such as a computer monitor, for displaying data and/or graphical user interfaces. The at least one computing device may also include a Global Positioning System (GPS) hardware device for determining a particular location of the computing device, an input device, such as a camera, a keyboard or a pointing device (e.g., a mouse, trackball, pen, or touch screen) to enter data into or interact with graphical and/or other types of user interfaces. In an exemplary embodiment, the display and the input device may be incorporated together as a touch screen of the smartphone or tablet computer.

The at least one computing device may display on the display a graphical user interface (or GUI) to generate a graphical user interface on the display. The graphical user interface may be provided by an application. The graphical user interface enables a user of the at least one computing device to interact with the application.

The application may be a component of an application and/or service executable by the at least one computing device. For example, the application may be a single unit of deployable executable code or a plurality of units of deployable executable code. According to one aspect, the application may include one component that may be a web application, a native application, and/or a mobile application (e.g., an app) downloaded from a digital distribution application platform that allows users to browse and download applications developed with mobile software development kits (SDKs) including the App Store and GOOGLE PLAY®, among others.

Figure 2:
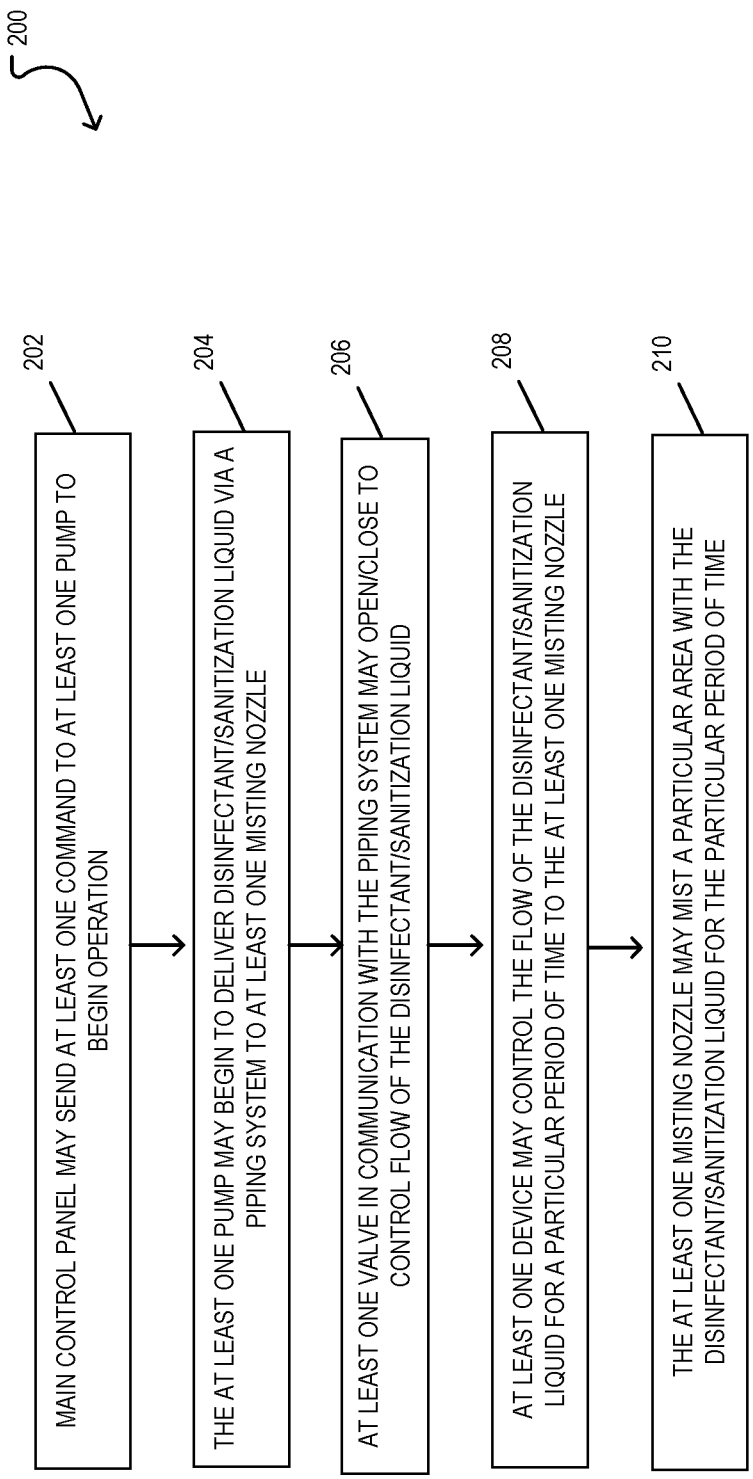
FIG. 2 illustrates a flowchart for sanitizing at least one zone, region, or area according to an example embodiment.

FIG. 2 illustrates a flowchart of a process 200 for sanitizing at least one zone, region, or area according to an example embodiment. In step 202, the main control panel 110 sends at least one command to the at least one pump 106 to begin operation. In step 204, the at least one pump 106 may begin to deliver the disinfectant/sanitization solution via the piping system 120 to at least one misting nozzle 116.

In step 206, the at least one valve 108 in communication with the piping system 120 may open or close to control flow of the disinfectant/sanitization solution. In step 208, the at least one device 114 may control the flow of the disinfectant/sanitization solution for a particular period of time to the at least one misting nozzle 116. In step 210, the at least one misting nozzle 116 in communication with the piping system 120 and the at least one valve 108 may mist or fog a particular region, zone, or area 118 with the disinfectant/sanitization solution for the particular period of time.

FIG. 3 illustrates an example computing system 300 that may implement various systems, such as the sanitization system 100, and the methods discussed herein, such as process 200. A general purpose computer system 300 is capable of executing a computer program product to execute a computer process. Data and program files may be input to the computer system 300, which reads the files and executes the programs therein. Some of the elements of a general purpose computer system 300 are shown in FIG. 3 wherein a processor 302 is shown having an input/output (I/O) section 304, a central processing unit (CPU) 306, and a memory section 308. There may be one or more processors 302, such that the processor 302 of the computer system 300 comprises a single central-processing unit 306, or a plurality of processing units, commonly referred to as a parallel processing environment. The computer system 300 may be a conventional computer, a server, a distributed computer, or any other type of computer, such as one or more external computers made available via a cloud computing architecture. The presently described technology is optionally implemented in software devices loaded in memory 308, stored on a configured DVD/CD-ROM 310 or storage unit 312, and/or communicated via a wired or wireless network link 314, thereby transforming the computer system 300 in FIG. 3 to a special purpose machine for implementing the described operations.

The memory section 308 may be volatile media, nonvolatile media, removable media, non-removable media, and/or other media or mediums that can be accessed by a general purpose or special purpose computing device. For example, the memory section 308 may include non-transitory computer storage media and communication media. Non-transitory computer storage media further may include volatile, nonvolatile, removable, and/or non-removable media implemented in a method or technology for the storage (and retrieval) of information, such as computer/machine-readable/executable instructions, data and data structures, engines, program modules, and/or other data. Communication media may, for example, embody computer/machine-readable/executable, data structures, program modules, algorithms, and/or other data. The communication media may also include an information delivery technology. The communication media may include wired and/or wireless connections and technologies and be used to transmit and/or receive wired and/or wireless communications.

The I/O section 304 is connected to one or more user-interface devices (e.g., a keyboard 316 and a display unit 318), a disc storage unit 312, and a disc drive unit 320. Generally, the disc drive unit 320 is a DVD/CD-ROM drive unit capable of reading the DVD/CD-ROM medium 310, which typically contains programs and data 322. Computer program products containing mechanisms to effectuate the systems and methods in accordance with the presently described technology may reside in the memory section 304, on a disc storage unit 312, on the DVD/CD-ROM medium 310 of the computer system 300, or on external storage devices made available via a cloud computing architecture with such computer program products, including one or more database management products, web server products, application server products, and/or other additional software components. Alternatively, a disc drive unit 320 may be replaced or supplemented by another storage medium drive unit. The network adapter 324 is capable of connecting the computer system 300 to a network via the network link 314, through which the computer system can receive instructions and data. Examples of such systems include personal computers, Intel or PowerPC-based computing systems, AMD-based computing systems, ARM-based computing systems, and other systems running a Windows-based, a UNIX-based, or other operating system. It should be understood that computing systems may also embody devices such as Personal Digital Assistants (PDAs), mobile phones, tablets or slates, multimedia consoles, gaming consoles, set top boxes, etc.

When used in a LAN-networking environment, the computer system 300 is connected (by wired connection and/or wireles sly) to a local network through the network interface or adapter 324, which is one type of communications device. When used in a WAN-networking environment, the computer system 300 typically includes a modem, a network adapter, or any other type of communications device for establishing communications over the wide area network. In a networked environment, program modules depicted relative to the computer system 300 or portions thereof, may be stored in a remote memory storage device. It is appreciated that the network connections shown are examples of communications devices for and other means of establishing a communications link between the computers may be used.

In an example implementation, source code executed by the computing device, a plurality of internal and external databases, source databases, and/or cached data on servers are stored in memory of the computing device, or other storage systems, such as the disk storage unit 312 or the DVD/CD-ROM medium 310, and/or other external storage devices made available and accessible via a network architecture. The source code executed by the computing device may be embodied by instructions stored on such storage systems and executed by the processor 302.

Some or all of the operations described herein may be performed by the processor 302, which is hardware. Further, local computing systems, remote data sources and/or services, and other associated logic represent firmware, hardware, and/or software configured to control operations of the sanitization system 100 and/or other components. Such services may be implemented using a general purpose computer and specialized software (such as a server executing service software), a special purpose computing system and specialized software (such as a mobile device or network appliance executing service software), or other computing configurations. In addition, one or more functionalities disclosed herein may be generated by the processor 302 and a user may interact with a Graphical User Interface (GUI) using one or more user-interface devices (e.g., the keyboard 316, the display unit 318, and the user devices 304) with some of the data in use directly coming from online sources and data stores. The system set forth in FIG. 3 is but one possible example of a computer system that may employ or be configured in accordance with aspects of the present disclosure.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon executable instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may include, but is not limited to, magnetic storage medium, optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic executable instructions.

The description above includes example systems, methods, techniques, instruction sequences, and/or computer program products that embody techniques of the present disclosure. However, it is understood that the described disclosure may be practiced without these specific details.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A method comprising:

sending, by at least one processor, a command to at least one pump to begin operation, the command sent from an intelligent programmable control panel associated with a building automation system that receives operation information from an external computing device to provide the command;

delivering, by the at least one pump connected to at least one storage tank, disinfectant/sanitization solution to kill viruses comprising coronaviruses and influenza viruses via a piping system to at least one misting nozzle, the at least one misting nozzle sized according to a hydraulic design and a flow demand calculation based on an area of a zone, height, pipe sizes, fittings, and friction loss of the solution flowing to the at least one misting nozzle to be atomized;

opening or closing at least one low voltage electromagnetic solenoid valve in communication with the piping system to control flow of the disinfectant/sanitization solution;

controlling the flow of the disinfectant/sanitization solution by at least one timed opening device to the at least one misting nozzle for a particular period of time; and in response to the command, misting a particular zone of at least one zone with the disinfectant/sanitization solution by the at least one misting nozzle for the particular period of time, the misting having design density to cover the particular zone each zone having respective timed commands for the particular period of time for the at least one timed opening device and each of the at least one misting nozzle in the particular zone to control the flow of the disinfectant/sanitization solution.

2. The method of claim 1, further comprising providing power to the at least one pump using at least one pump controller in communication with the at least one pump.

3. The method of claim 1, further comprising providing commands from the control panel to the at least one device to control the flow of the disinfectant/sanitization solution.

4. The method of claim 1, further comprising preventing debris from passing through the piping system using at least one filter.

5. The method of claim 1, wherein the particular zone area is located in a building.

6. The method of claim 1, wherein the disinfectant/sanitization solution is approved by the United States Environmental Protection Agency (EPA).

7. The method of claim 1, further comprising controlling the flow of the disinfectant/sanitization solution for the particular period of time to the at least one misting nozzle using the external computing device.

8. A non-transitory computer-readable storage medium, having instructions stored thereon that, when executed by a computing device causes the computing device to perform operations, the operations comprising:

sending, by at least one processor, a command to at least one pump to begin operation, the command sent from an intelligent programmable control panel associated with a building automation system that receives operation information from an external computing device to provide the command;

delivering, by the at least one pump connected to at least one storage tank, disinfectant/sanitization solution to kill viruses comprising coronaviruses and influenza viruses via a piping system to at least one misting nozzle, the at least one misting nozzle sized according to a hydraulic design and a flow demand calculation based on an area of a zone, height, pipe sizes, fittings, and friction loss of the solution flowing to the at least one misting nozzle to be atomized;

opening or closing at least one low voltage electromagnetic solenoid valve in communication with the piping system to control flow of the disinfectant/sanitization solution;

controlling the flow of the disinfectant/sanitization solution by at least one timed opening device to the at least one misting nozzle for a particular period of time; and in response to the command, misting a particular zone of at least one zone with the disinfectant/sanitization solution by the at least one misting nozzle for the particular period of time, the misting having design density to cover the particular zone area, the particular area each zone having respective timed commands for the particular period of time for the at least one timed opening device and each of the at least one misting nozzle in the particular zone to control the flow of the disinfectant/sanitization solution.

9. The non-transitory computer-readable medium of claim 8, the operations further comprising providing power to the at least one pump using at least one pump controller in communication with the at least one pump.

10. The non-transitory computer-readable medium of claim 8, the operations further comprising providing commands from the control panel to the at least one device to control the flow of the disinfectant/sanitization solution.

11. The non-transitory computer-readable medium of claim 8, the operations further comprising preventing debris from passing through the piping system using at least one filter.

12. The non-transitory computer-readable medium of claim 8, wherein the particular zone is located in a building.

13. The non-transitory computer-readable medium of claim 8, wherein the disinfectant/sanitization solution is approved by the United States Environmental Protection Agency (EPA).

14. The non-transitory computer-readable medium of claim 8, the operations further comprising controlling the flow of the disinfectant/sanitization solution for the particular period of time to the at least one misting nozzle using the external computing device.

\* \* \* \* \*